US010902585B2

(12) United States Patent
Nett

(10) Patent No.: US 10,902,585 B2
(45) Date of Patent: Jan. 26, 2021

(54) SYSTEM AND METHOD FOR AUTOMATED ANGIOGRAPHY UTILIZING A NEURAL NETWORK

(71) Applicant: General Electric Company, Schenectady, NY (US)

(72) Inventor: Brian Edward Nett, Wauwatosa, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 361 days.

(21) Appl. No.: 15/924,706

(22) Filed: Mar. 19, 2018

(65) Prior Publication Data

US 2019/0287239 A1  Sep. 19, 2019

(51) Int. Cl.
*G06T 7/00* (2017.01)
*G06T 7/11* (2017.01)
*G16H 30/40* (2018.01)
*G06N 3/08* (2006.01)

(52) U.S. Cl.
CPC ............ *G06T 7/0012* (2013.01); *G06N 3/08* (2013.01); *G06T 7/11* (2017.01); *G16H 30/40* (2018.01); *G06T 2207/10076* (2013.01); *G06T 2207/10081* (2013.01); *G06T 2207/20081* (2013.01); *G06T 2207/20084* (2013.01); *G06T 2207/30101* (2013.01)

(58) Field of Classification Search
None
See application file for complete search history.

(56) References Cited

U.S. PATENT DOCUMENTS

| 9,589,374 | B1 * | 3/2017 | Gao | G06T 11/008 |
| 2008/0287803 | A1 * | 11/2008 | Li | A61B 8/466 |
| | | | | 600/466 |
| 2018/0310992 | A1 * | 11/2018 | Baldauf | A61B 90/37 |
| 2019/0287239 | A1 * | 9/2019 | Nett | G06N 3/08 |

OTHER PUBLICATIONS

Lell, Michael M., et al.; "New Techniques in CT Angiography", Clinical Applications of Vascular Imaging, vol. 26, Special Issue, Oct. 2006, pp. S45-S63.
Mendrik, Adrienne, et al.; "Automatic Segmentation of Intracranial Arteries and Veins in Four-Dimensional Cerebral CT Perfusion Scans", Medical Physics, vol. 37, No. 6, Jun. 2010.
Han, Dongjin, et al.; "Automatic Coronary Artery Segmentation Using Active Search for Branches and Seemingly Disconnected Vessel Segments from Coronary CT Angiography", PLOS ONE, Aug. 2016, pp. 1-24.
Nardelli, P., et al.; "Deep-Learning Strategy for Pulmonary Artery-Vein Classification of Non-Contrast CT Images", 2017 IEEE 14th International Symposium on Biomedical Imaging (ISBI 2017); pp. 384-387.

* cited by examiner

*Primary Examiner* — Tahmina N Ansari
(74) *Attorney, Agent, or Firm* — Fletcher Yoder, P.C.

(57) ABSTRACT

A method for analyzing computed tomography angiography (CTA) data is provided. The method includes receiving, at a processor, three-dimensional (3D) CTA data. The method also includes automatically, via the processor, detecting objects of interest within the 3D CTA data. The method further includes generating, via the processor, a CTA image volume that only includes the objects of interest.

18 Claims, 5 Drawing Sheets

SYSTEM AND METHOD FOR AUTOMATED ANGIOGRAPHY UTILIZING A NEURAL NETWORK

BACKGROUND

The subject matter disclosed herein relates to medical imaging and, in particular, to a system and method for performing automated computed tomography angiography.

Volumetric medical imaging technologies use a variety of techniques to gather three-dimensional information about the body. For example, computed tomography (CT) imaging system measure the attenuation of X-ray beams passed through a patient from numerous angles. Based upon these measurements, a computer is able to reconstruct images of the portions of a patient's body responsible for the radiation attenuation. As will be appreciated by those skilled in the art, these images are based upon separate examination of a series of angularly displaced measurements. It should be pointed out that a CT system produces data that represent the distribution of linear attenuation coefficients of the scanned object. The data are then reconstructed to produce an image that is typically displayed on a screen, and may be printed or reproduced on film.

For example, in the field of CT angiography (CTA), vasculature and other circulatory system structures may be imaged, typically by administration of a radio-opaque dye prior to imaging. Visualization of the CTA data typically is performed in a two-dimensional manner, i.e., slice-by-slice, or in a three-dimensional manner, i.e., volume visualization, which allows the data to be analyzed for vascular pathologies. For example, the data may be analyzed for aneurysms, vascular calcification, renal donor assessment, stent placement, vascular blockage, and vascular evaluation for sizing and/or runoff. Once a pathology is located, quantitative assessments of the pathology may be made of the on the original two-dimensional slices.

The CTA process may include processes for segmenting structures in the image data, such as the vasculature and/or the bone structures. Such segmentation typically involves identifying which voxels of the image data are associated with a particular structure or structures of interest. Segmented structures may then be viewed outside of the context of the remainder of the image data or may be masked from the remainder of the image data to allow otherwise obstructed structure to be viewed. For example, in CTA, segmentation may be performed to identify all voxels associated with the vasculature, allowing the entire circulatory system in the imaged region to be extracted and viewed. Similarly, all voxels of the bone structures may be identified and masked, or subtracted, from the image data, allowing vasculature and/or other structures which might otherwise be obscured by the relatively opaque bone structures to be observed during subsequent visualization.

However, segmentation of vasculature and bone structures may be complicated by a variety of factors. For example, in CTA, overlapping image intensities, close proximity of imaged structures, limited detector resolution, slow imaging volume coverage (i.e., slow scan speed), calcification, complexity of the anatomic regions and sub-regions, imperfect contrast timing, and interventional devices may make the identification and segmentation of bone and vascular structures difficult. Because of these complicating factors, image visualization specialists are utilized to manually intervene to generate images for radiologists. For example, these image visualization specialists both manually detect and/or remove structures (e.g., vein, artery, etc.) from the reconstructed CT data and reformat (e.g., transform or sample) the image volume to generate two-dimensional (2D) images. The utilization of these image visualization specialist is labor intensive and costly. In addition, on lower tier scanners (i.e. less than 16 rows) it is physically impossible to acquire a vascular study of the arteries without contamination of the veins given the required acquisition time. It may, therefore, be desirable to automate the detection and/or removal of structures from the reconstructed CT data as well as reformatting of the image volume in the CTA process.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In accordance with a first embodiment, a method for analyzing computed tomography angiography (CTA) data is provided. The method includes receiving, at a processor, three-dimensional (3D) CTA data. The method also includes automatically, via the processor, detecting objects of interest within the 3D CTA data. The method further includes generating, via the processor, a CTA image volume that only includes the objects of interest.

In accordance with a second embodiment, a method for analyzing computed tomography angiography (CTA) data is provided. The method includes receiving, at a processor, four-dimensional (4D) CTA data. The method also includes generating, via the processor, non time-resolved CTA data from the 4D CTA data. The method further includes generating, via the processor, a first set of 4D images including veins only from the 4D CTA data. The method still further includes generating, via the processor, a second set of 4D images including arteries only from the 4D CTA data. The method yet further includes training, via the processor, a convolutional neural network utilizing the non time-resolved CTA data, the first set of 4D images, and the second set of 4D images to generate a trained convolutional neural network.

In accordance with a third embodiment, a method for analyzing computed tomography angiography (CTA) data is provided. The method includes obtaining, at the processor, past review types utilized by users, image reformat rendering angles relative to computed tomography (CT) system landmarks for a respective past review type selected by the users, and image reformat rendering angles relative to anatomical landmarks for the respective past review type selected by the users. The method also includes training, via the processor, the convolutional neural network utilizing the past review types utilized by users, the image reformat rendering angles relative to CT system landmarks for the respective past review type selected by the users, and the image reformat rendering angles relative to anatomical landmarks for the respective past review type selected by the users to generate a trained convolutional neural network.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
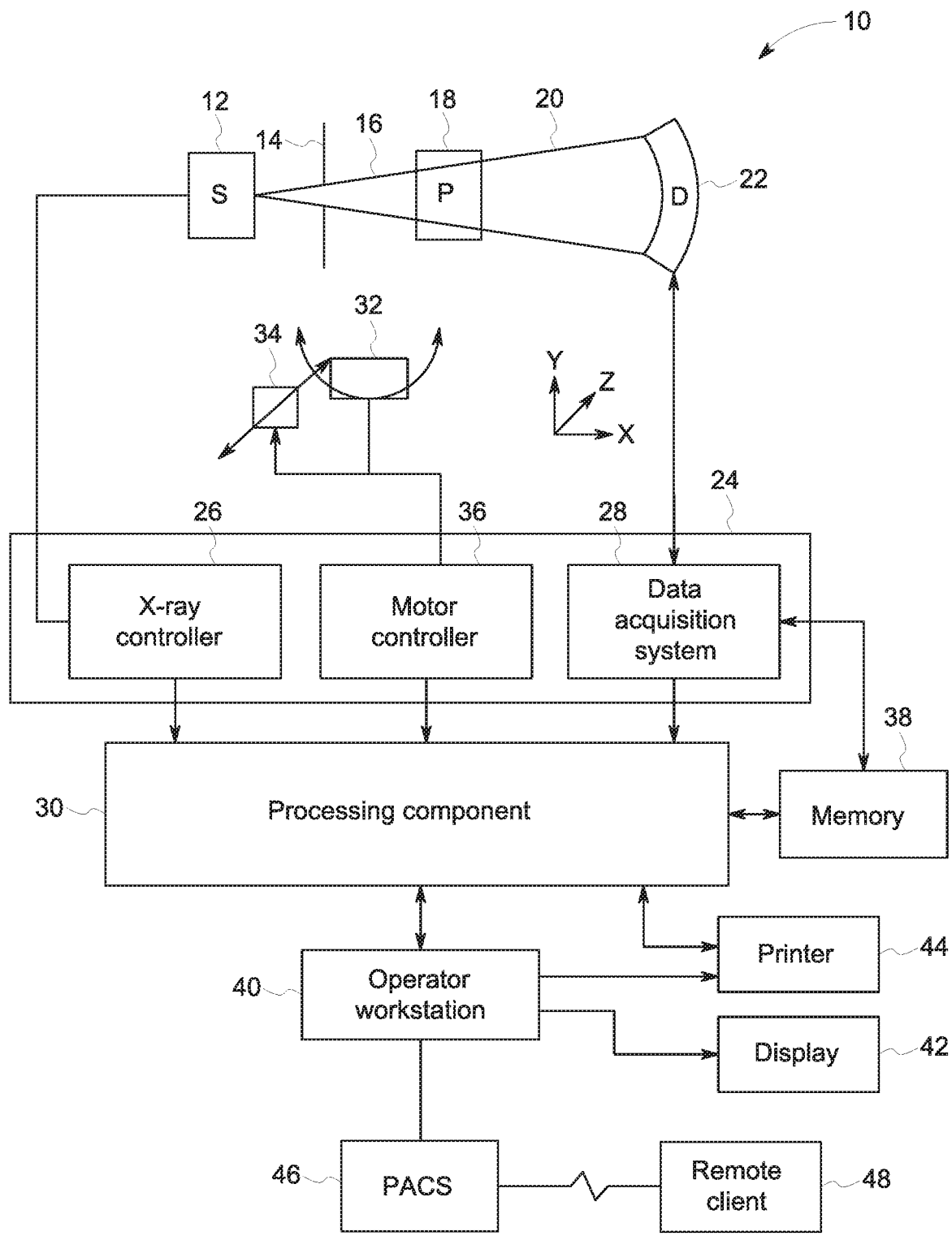
FIG. 1 is a block diagram depicting components of a computed tomography (CT) imaging system, in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Disclosed herein are systems and methods for analyzing computed tomography angiography (CTA) data. In particular, the disclosed embodiments utilize processing circuitry (e.g., of a console or computer of a computed tomography (CT) imaging system) to automatically isolate (via detection and/or removal) an object of interest (e.g., vein, artery, soft tissue, bone, etc.) from three-dimensional (3D) CTA data and to automatically (i.e., without user interaction or input) reformat an imaging volume (e.g., only having the object of interest) to generate two-dimensional (2D) images. In certain embodiments, a neural network may be trained on four-dimensional (4D) CTA data to learn how to automatically detect or remove objects from reconstructed 3D CTA data to generate image volumes. In addition, a neural network may be trained to identify an object of interest and desired orientation of a particular view based on past review types utilized by users and their respective image reformat rendering angles relative to CT system landmarks and/or anatomical landmarks utilized in those past review types. The automatization of the isolation of an object of interest and reformatting of CTA data enables analysis and visualization of CTA data on lower tier scanners (e.g., with less than 16 row scanners) having a slow volume coverage and/or situations with imperfect contrast timing. In addition, on fast volumetric coverage systems, the disclosed techniques reduce venous contamination due to imperfect contrast timing. Further, this automatization reduces both the time and costs associated with utilizing visualization specialists in generating CTA data for analysis.

With this in mind, an example of a CT imaging system 10 designed to acquire X-ray attenuation data at a variety of views around a patient (or other subject or object of interest) and suitable for automated angiography (i.e., automated object identification and reformatting) is provided in FIG. 1. Although the techniques below are discussed in the context of a CT imaging system, the techniques may also be utilized in other imaging systems (e.g., magnetic resonance (MR) imaging system, X-ray system, ultrasound system, positron emission tomography (PET) system, etc.). In the embodiment illustrated in FIG. 1, imaging system 10 includes a source of X-ray radiation 12 positioned adjacent to a collimator 14. The X-ray source 12 may be an X-ray tube, a distributed X-ray source (such as a solid-state or thermionic X-ray source) or any other source of X-ray radiation suitable for the acquisition of medical or other images.

The collimator 14 permits X-rays 16 to pass into a region in which a patient 18, is positioned. In the depicted example, the X-rays 16 are collimated to be a cone-shaped beam, i.e., a cone-beam that passes through the imaged volume. A portion of the X-ray radiation 20 passes through or around the patient 18 (or other subject of interest) and impacts a detector array, represented generally at reference numeral 22. Detector elements of the array produce electrical signals that represent the intensity of the incident X-rays 20. These signals are acquired and processed to reconstruct images of the features within the patient 18.

Source 12 is controlled by a system controller 24, which furnishes both power, and control signals for CT examination sequences, including acquisition of 2D localizer or scout images used to identify anatomy of interest within the patient for subsequent scan protocols. In the depicted embodiment, the system controller 24 controls the source 12 via an X-ray controller 26 which may be a component of the system controller 24. In such an embodiment, the X-ray controller 26 may be configured to provide power and timing signals to the X-ray source 12.

Moreover, the detector 22 is coupled to the system controller 24, which controls acquisition of the signals generated in the detector 22. In the depicted embodiment, the system controller 24 acquires the signals generated by the detector using a data acquisition system 28. The data acquisition system 28 receives data collected by readout electronics of the detector 22. The data acquisition system 28 may receive sampled analog signals from the detector 22 and convert the data to digital signals for subsequent processing by a processor 30 discussed below. Alternatively, in other embodiments the digital-to-analog conversion may be performed by circuitry provided on the detector 22 itself. The system controller 24 may also execute various signal processing and filtration functions with regard to the acquired image signals, such as for initial adjustment of dynamic ranges, interleaving of digital image data, and so forth.

In the embodiment illustrated in FIG. 1, system controller 24 is coupled to a rotational subsystem 32 and a linear positioning subsystem 34. The rotational subsystem 32 enables the X-ray source 12, collimator 14 and the detector 22 to be rotated one or multiple turns around the patient 18, such as rotated primarily in an x, y-plane about the patient. It should be noted that the rotational subsystem 32 might include a gantry upon which the respective X-ray emission and detection components are disposed. Thus, in such an embodiment, the system controller 24 may be utilized to operate the gantry.

The linear positioning subsystem 34 may enable the patient 18, or more specifically a table supporting the patient, to be displaced within the bore of the CT system 10, such as in the z-direction relative to rotation of the gantry. Thus, the table may be linearly moved (in a continuous or step-wise fashion) within the gantry to generate images of particular areas of the patient 18. In the depicted embodiment, the system controller 24 controls the movement of the rotational subsystem 32 and/or the linear positioning subsystem 34 via a motor controller 36.

In general, system controller 24 commands operation of the imaging system 10 (such as via the operation of the source 12, detector 22, and positioning systems described above) to execute examination protocols and to process acquired data. For example, the system controller 24, via the systems and controllers noted above, may rotate a gantry supporting the source 12 and detector 22 about a subject of interest so that X-ray attenuation data may be obtained at one or more views relative to the subject. In the present context, system controller 24 may also include signal processing circuitry, associated memory circuitry for storing programs and routines executed by the computer (such as routines for executing image visualization techniques that enable automatic (i.e., without user intervention) detection of objects of interests and reformatting of 2D images from an imaging volume as described herein), as well as configuration parameters, image data, reconstructed images, and so forth.

In the depicted embodiment, the image signals acquired and processed by the system controller 24 are provided to a processing component 30 for reconstruction of images in accordance with the presently disclosed algorithms. The processing component 30 may be one or more general or application-specific microprocessors. The data collected by the data acquisition system 28 may be transmitted to the processing component 30 directly or after storage in a memory 38. Any type of memory suitable for storing data might be utilized by such an exemplary system 10. For example, the memory 38 may include one or more optical, magnetic, and/or solid-state memory storage structures. Moreover, the memory 38 may be located at the acquisition system site and/or may include remote storage devices for storing data, processing parameters, and/or routines for image reconstruction as described herein.

The processing component 30 may be configured to receive commands and scanning parameters from an operator via an operator workstation 40, typically equipped with a keyboard and/or other input devices. An operator may control the system 10 via the operator workstation 40. Thus, the operator may observe the reconstructed images and/or otherwise operate the system 10 using the operator workstation 40. For example, a display 42 coupled to the operator workstation 40 may be utilized to observe the reconstructed images and to control imaging. Additionally, the images may also be printed by a printer 44 which may be coupled to the operator workstation 40.

Further, the processing component 30 and operator workstation 40 may be coupled to other output devices, which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 40 may also be coupled to a picture archiving and communications system (PACS) 46. PACS 46 may in turn be coupled to a remote client 48, radiology department information system (RIS), hospital information system (HIS) or to an internal or external network, so that others at different locations may gain access to the raw or processed image data.

While the preceding discussion has treated the various exemplary components of the imaging system 10 separately, these various components may be provided within a common platform or in interconnected platforms. For example, the processing component 30, memory 38, and operator workstation 40 may be provided collectively as a general or special purpose computer or workstation configured to operate in accordance with the aspects of the present disclosure. In such embodiments, the general or special purpose computer may be provided as a separate component with respect to the data acquisition components of the system 10 or may be provided in a common platform with such components. Likewise, the system controller 24 may be provided as part of such a computer or workstation or as part of a separate system dedicated to image acquisition.

As discussed herein, the system 10 of FIG. 1 may be used to conduct a computed tomography (CT) scan to acquire 3D or 4D CTA data from a patient 18 or object. The 4D CTA may be utilized by the system to train a neural network (e.g., convolutional neural network) or machine learning algorithm to detect objects of interest within 3D CTA data. In addition, past activities or review types (and the associated image reformat rendering angles utilized relative to CT system or anatomical landmarks) conducted by advanced visualization specialists may be utilized to train the neural network or machine learning algorithm to learn anatomical locations and reformat planes for utilization in identifying the location of objects of interests (e.g., vessels) and a desired orientation of view an CTA imaging volume derived from the 3D CTA data. The neural network or machine learning algorithm may enable the system to automatically detect object of interests from 3D CTA data and to automatically reformat the CTA imaging volume to generate desired 2D images of only the object of interest.

Figure 2:
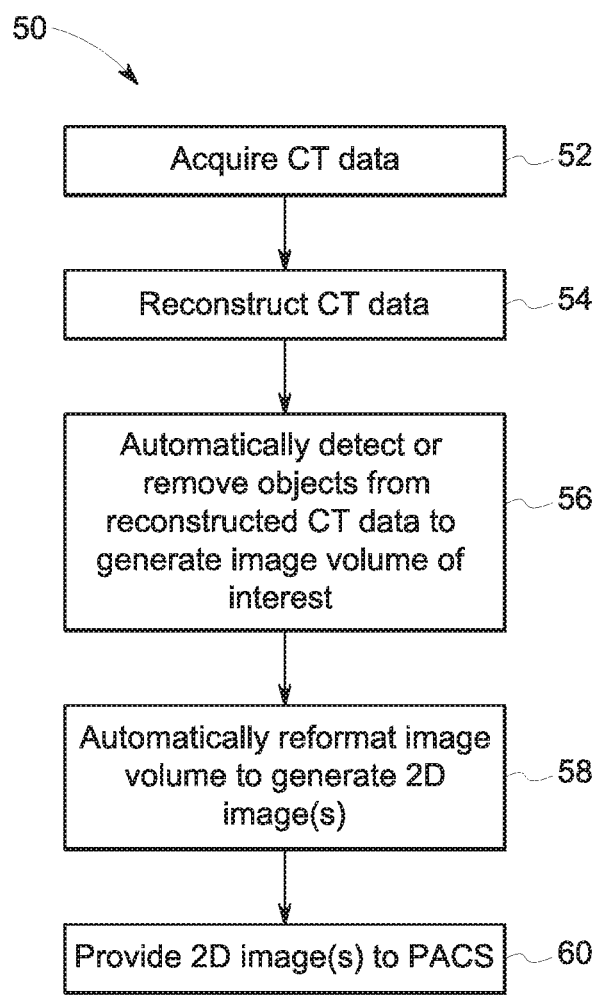
FIG. 2 is a flow chart of an embodiment of a method for analyzing computed tomography angiography (CTA) data.

FIG. 2 is a flow chart of an embodiment of a method 50 for analyzing CTA data. Some or all of the steps of the method 50 may be performed by the system controller 24, processing component 30, and/or operator workstation 40. One or more steps of the illustrated method 50 may performed in a different order from the order depicted in FIG. 2 and/or simultaneously. The method 50 includes acquiring CT data (e.g., 3D CTA data) of a patient or object (e.g., utilizing system 10) (block 52). The method 50 also includes reconstructing the CT data (block 54).

The method 50 further includes automatically (i.e., without user interaction) detecting or identifying (e.g., via segmentation) an object of interest (e.g., artery, vein, bone, or soft tissue) from the reconstructed CT data to generate an image volume of interest (e.g., 3D CTA image volume) (block 56). In certain embodiments, the method 50 includes removing other objects other than the object of interest from the reconstructed CT data. For example, if the object of interest is an artery, veins, bone, and/or soft tissue may be removed from the image volume. The detection and/or removal of objects may be automatically executed via a trained neural network or machine learning algorithm. In certain embodiments, the trained neural network may be a convolutional neural network (CNN) that utilizes cross-correlation in analyzing imaging data. The CNN utilizes different multilayer perceptrons that require minimal pre-processing. As a result, the CNN learns the filters or weights to be utilized (enabling independence from prior knowledge and human effort). In addition, the CNN shares weights that are utilized in the convolutional layers to reduce memory footprint and improve performance. The training of the neural network for object detection or identification is described in greater detail below.

The method 50 yet further includes automatically (i.e., without user interaction) reformatting (i.e., sampling or transforming) or planar reformatting the image volume (e.g., CTA image volume) to generate one or more 2D images (e.g., for a specific review type) that include only the object of interest (block 58). Reformatting may utilize volume rendering, directional maximum intensity projection (MIP), or other visualization technique in generating the 2D images. The image reformat rendering angles of the 2D images may be set relative to global CT system landmarks (e.g., axial, coronal, or sagittal MIPs). In addition, the image reformat rendering angles of the 2D images may be set relative to anatomical landmarks (e.g., volume rendering of circle of Willis, left carotid, right carotid, etc.). The reformatting or planar reformatting may be automatically executed via a trained neural network or machine learning algorithm. The training of the neural network for reformatting is described in greater detail below. The method 50 even further includes providing the one or more generated 2D images to PACS (block 60) for visualization (e.g., in a radiologist report).

Figure 3:
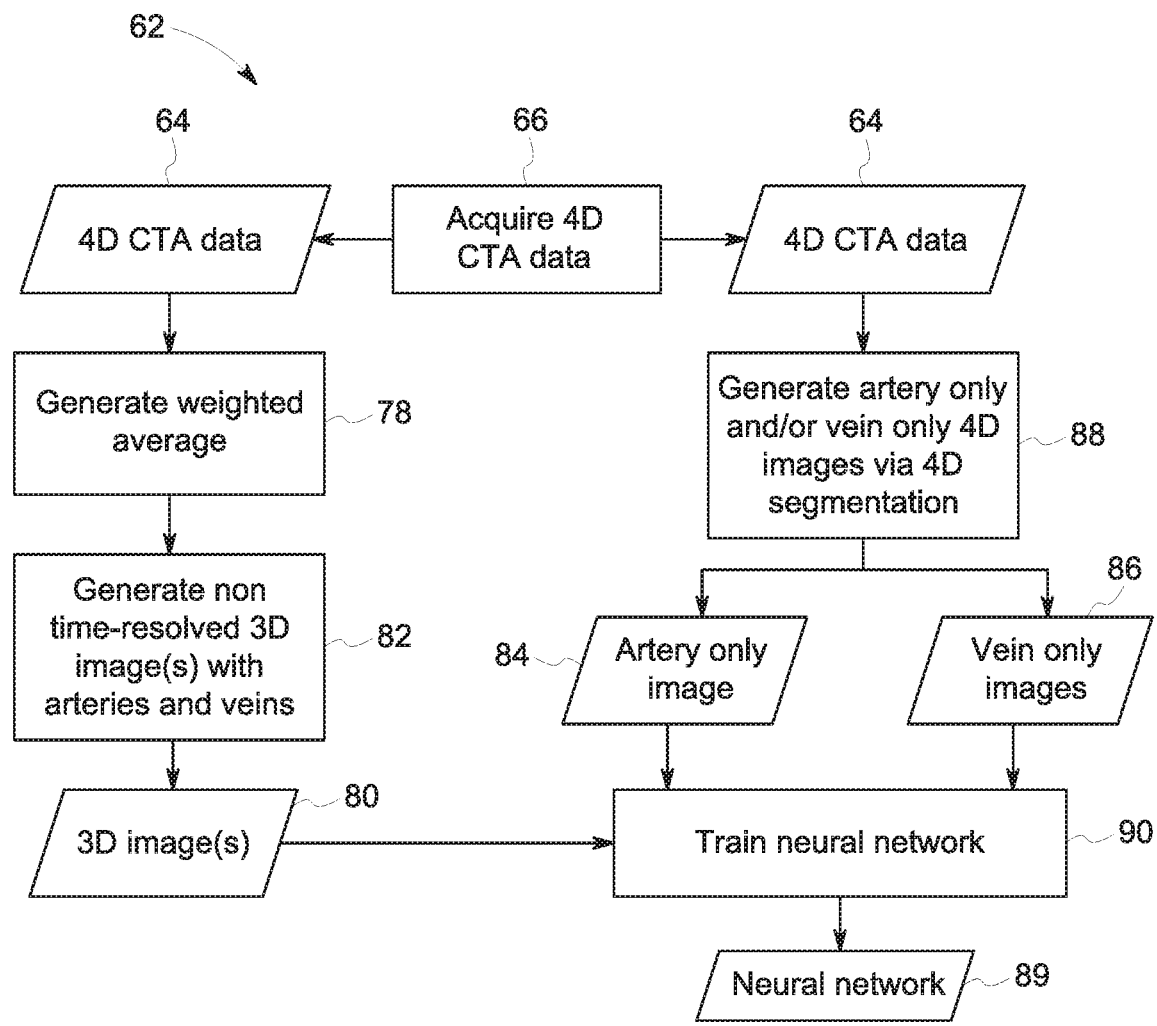
FIG. 3. is a flow chart of an embodiment of a method for training a neural network with four-dimensional (4D) CTA data for utilization in detecting or removing objects from three-dimensional (3D) CTA data.
Figure 4:
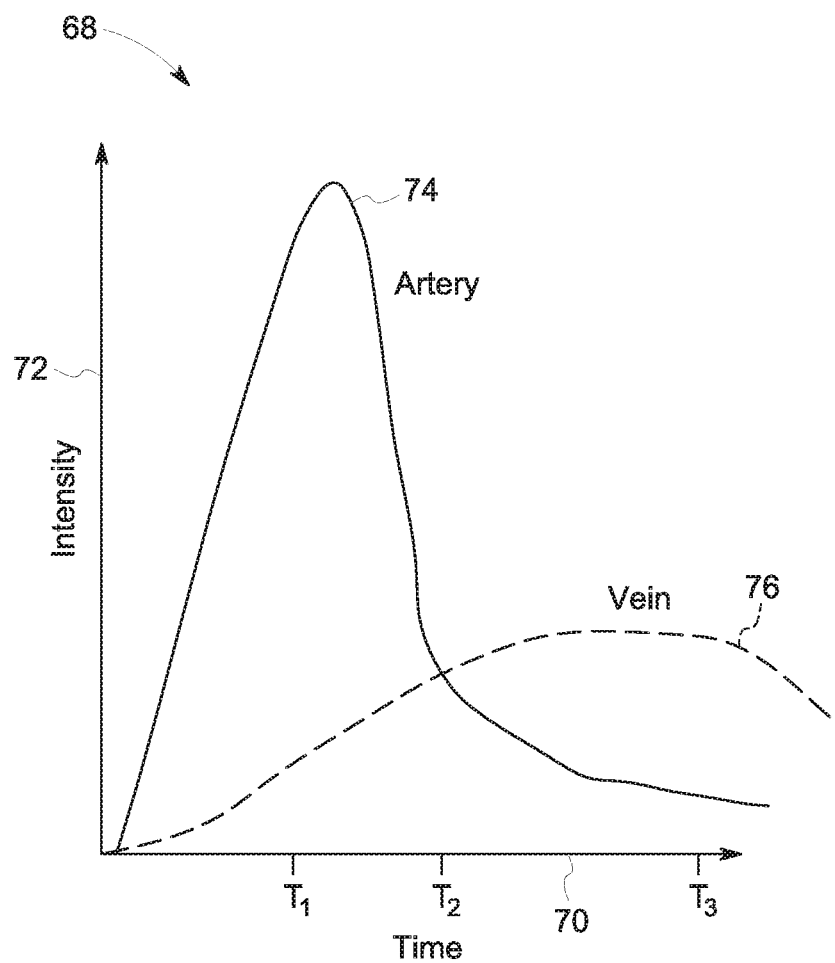
FIG. 4 is a graphical representation of CTA data for a given voxel location over time.

FIG. 3 is a flow chart of an embodiment of a method 62 for training a neural network 89 with four-dimensional (4D) CTA data for utilization in detecting or removing objects from three-dimensional (3D) CTA data. Some or all of the steps of the method 62 may be performed by the system controller 24, processing component 30, and/or operator workstation 40. One or more steps of the illustrated method 62 may performed in a different order from the order depicted in FIG. 3 and/or simultaneously. The method 62 includes acquiring or obtaining 4D CTA data 64 of a patient (e.g., utilizing system 10) (block 66). 4D CTA data includes x, y, and z data in conjunction with time. FIG. 4 is a graphical representation 68 of CTA data for a given voxel location over time (i.e., 4D CTA data). The graph 68 includes an x-axis 70 representing time and a y-axis 72 representing CT intensity (e.g., due to the presence of a contrast agent). CTA may be collected at various times ($T_1$, $T_2$, $T_3$, etc.) for the given voxel location to form the 4D CTA data. Plot 74 represents the signal from artery and plot 76 represents the signal from the vein. As depicted in FIG. 4, initially (e.g., at $T_1$) the majority of the contribution to the intensity is from the artery (where most of the contrast agent is located). Then, (e.g., at $T_2$) the contribution to the intensity is split between both the artery and the vein (due to the presence of the contrast agent in both). Finally, (e.g., at $T_3$) the majority of the contribution to the intensity is from the vein (where most of the contrast agent is located).

The method 62 includes generating a weighted average from acquired or obtained 4D CTA data (x, y, and z data in conjunction with time) (block 78). For example, the data points $T_1$, $T_2$, and $T_3$ may be given different weights, where the normalized weighted sum the weights may equal 1. In certain embodiments, data points that include the majority of intensity in the artery (e.g., $T_1$) may be given a higher weight than data points that include the majority of intensity in the vein (e.g., $T_3$). In other embodiments, data points that include the majority of intensity in the vein (e.g., $T_3$) may be given a higher weight than data points that include the majority of intensity in the artery (e.g., $T_1$). The method 62 also includes generating non-time resolved or static 3D CTA image(s) 80 with arteries and veins based on the weighted average of the 4D CTA data (block 82). Non-time resolved images are similar to images acquired in standard CT acquisition.

The method 62 further includes generating artery 84 and/or vein 86 only 4D images from the 4D CTA data (block 88). 4D segmentation techniques are utilized to generate the artery only images 84 and the vein only images 86. The 4D segmentation techniques identify different classes of tissues (e.g., vein, artery, soft tissue, or bone) in the 4D CTA data. The method 62 even further includes training a neural network 89 (e.g., CNN as described above) or machine learning algorithm to detect or identify (or remove) objects of interest (e.g., vein, artery, soft tissue, bone) from 3D CTA data (block 90). In certain embodiments, the neural network 89 is trained on the non-time resolved image(s) 80, artery only images 84, and vein only images 86. In other embodiments, the neural network 89 is trained on one or more of the non-time resolved image(s) 80, artery only images 84, and vein only images 86. The weights learned by the trained neural network 89 may be stored for the application of the trained neural network 89 to 3D CTA data.

Figure 5:
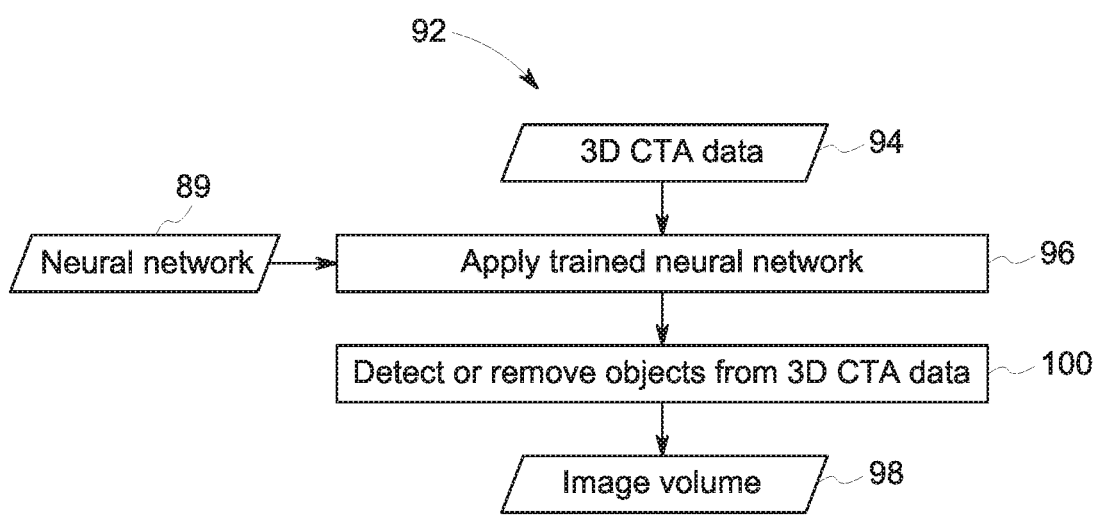
FIG. 5 is flow chart of an embodiment of a method for utilizing a trained neural network to detect or remove objects from 3D CTA data.

FIG. 5 is flow chart of an embodiment of a method 92 for utilizing the trained neural network 89 to detect or remove objects from 3D CTA data. Some or all of the steps of the method 92 may be performed by the system controller 24, processing component 30, and/or operator workstation 40. The method 92 includes applying the trained neural network 89 to the acquired 3D CTA data 94 from the patient (block 96). As noted above, the trained neural network 89 may utilize the weights learned during training to the 3D CTA data. The method 92 also includes automatically detecting or identifying (or removing) objects from the 3D CTA data (via the applied trained neural network 89) to generate a 3D CTA image volume 98 that only includes the object of interest (e.g., vein, artery, soft tissue, bone) (block 100).

Figure 6:
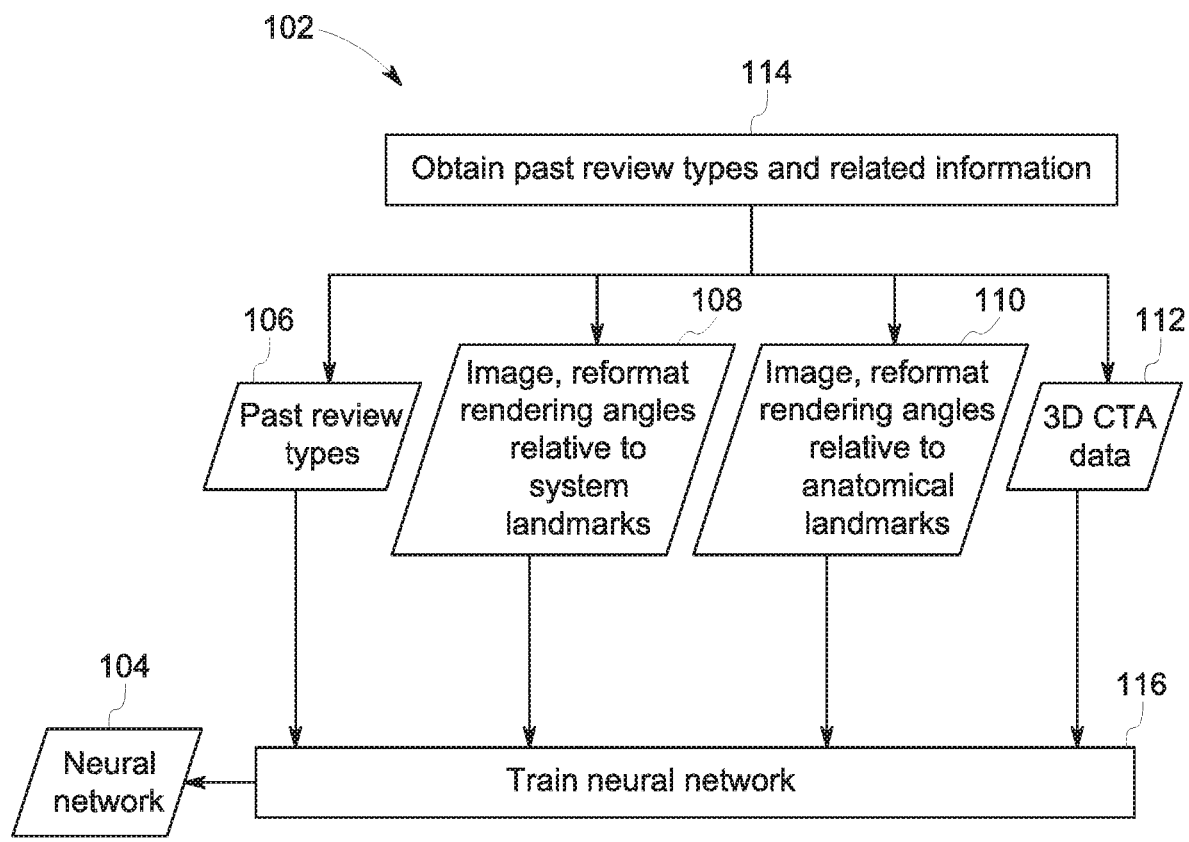
FIG. 6 is a flow chart of an embodiment of a method for training a neural network for utilization in reformatting an image volume.

FIG. 6 is a flow chart of an embodiment of a method 102 for training a neural network 104 for utilization in reformatting (e.g., planar reformatting) an image volume. Some or all of the steps of the method 92 may be performed by the system controller 24, processing component 30, and/or operator workstation 40. For a given CT protocol and review type, advanced visualization specialists or users manually determine image reformat rendering angles for an object interest in an image volume. In particular, the advanced visualization specialists set the image reformat rendering angles relative CT system landmarks (e.g., axial, coronal, and/or sagittal MIPs) and/or image reformat rendering angles relative to anatomical landmarks (e.g., volume rendering of the Circle of Willis, volume rendering of the left carotid, volume rendering of the right carotid, etc.) in generating the 2D images with only the object of interest.

Past review types 106, associated image reformat rendering angles 108 relative to system landmarks for these respective past review types, associated image reformat rendering angles 110 relative to anatomical landmarks for these respective past review types, and the 3D CTA data (imaging volumes) 112 utilized in these past review types may be monitored and stored for utilization in training the neural network 104 (e.g., CNN) or machine learning algorithm. The method 102 includes obtaining these past review types 106 and associated information (e.g., associated image reformat rendering angles 108, 110 and/or associated 3D CTA data 112) (block 114). The method 102 also includes training the neural network 104 (e.g., CNN) with past review types 106 image reformat rendering angles 108, 110, and/or associated 3D CTA data 112 (block 116). The neural network 104 learns anatomical locations and reformat planes as well identifies a location of an object of interest (e.g., vessel of interest) and the desired orientation of the view based on the review type. Thus, the trained neural network 104 when applied can automatically set the image reformat rendering angles relative to system landmarks and anatomical landmarks based on the CT protocol and review type.

Figure 7:
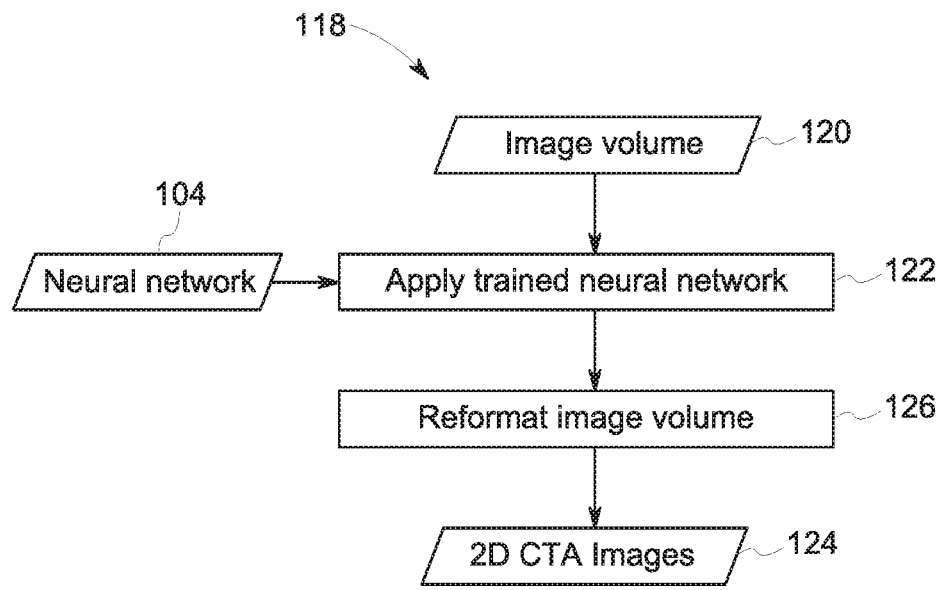
FIG. 7 is a flow chart of an embodiment of a method for utilizing a trained neural network to reformat an image volume.

FIG. 7 is a flow chart of an embodiment of a method 118 for utilizing the trained neural network 104 to reformat an image volume. Some or all of the steps of the method 92 may be performed by the system controller 24, processing component 30, and/or operator workstation 40. The method 118 includes applying the trained neural network 104 to an image volume (e.g., acquired 3D CTA data 94 from the patient) (block 122). The method 118 also includes automatically reformatting or planar reformatting the image volume (via the applied trained neural network 104) to generate 2D CTA images 124 that only include the object of interest (e.g., artery, vein, bone, soft tissue) for the CT protocol and review type (block 126).

Technical effects of the disclosed embodiments include providing systems and methods that automatically isolate (via detection and/or removal) an object of interest (e.g., vein, artery, soft tissue, bone, etc.) from 3D CTA data and automatically (i.e., without user interaction or input) reformat an imaging volume (e.g., only having the object of interest) to generate 2D CTA images. The automatization of the isolation of an object of interest and reformatting of CTA data enables analysis and visualization of CTA data on lower tier scanners (e.g., with less than 16 row scanners) having a slow volume coverage and/or situations with imperfect contrast timing. In addition, on fast volumetric coverage systems, the disclosed techniques reduce venous contamination due to imperfect contrast timing. Further, this automatization reduces both the time and costs associated with utilizing visualization specialists in generating CTA data for analysis.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for analyzing computed tomography angiography (CTA) data, comprising:

obtaining, at a processor, past review types utilized by users, image reformat rendering angles relative to computed tomography (CT) system landmarks for a respective past review type selected by the users, and image reformat rendering angles relative to anatomical landmarks for the respective past review type selected by the users;

training, via the processor, a convolutional neural network utilizing the past review types utilized by users, the image reformat rendering angles relative to CT system landmarks for the respective past review type selected by the users, and the image reformat rendering angles relative to anatomical landmarks for the respective past review type selected by the users to generate the trained convolutional neural network;

receiving, at the processor, three-dimensional (3D) CTA data;

automatically, via the processor, detecting objects of interest within the 3D CTA data, wherein automatically detecting the objects of interest within the CTA data comprises applying, via the processor, the trained convolutional neural network to the 3D CTA data to segment the objects of interest from the 3D CTA data;

generating, via the processor, a CTA image volume that only includes the objects of interest; and utilizing, via the processor, the trained convolutional neural network to automatically reformat the CTA image volume to generate one or more two-dimensional (2D) CTA images.

2. The method of claim 1, wherein the objects of interest comprise arteries, veins, soft tissue, or bone.

3. The method of claim 1, comprising:

receiving, at the processor, four-dimensional (4D) CTA data;

generating, via the processor, non time-resolved CTA data from the 4D CTA data;

generating, via the processor, a first set of 4D images including veins only from the 4D CTA data; and generating, via the processor, a second set of 4D images including arteries only from the 4D CTA data.

4. The method of claim 3, comprising training, via the processor, a convolutional neural network utilizing the non time-resolved CTA data, the first set of 4D images, and the second set of 4D images to generate the trained convolutional neural network.

5. The method of claim 3, comprising training, via the processor, a convolutional neural network utilizing the non time-resolved CTA data, the first set of 4D images, or the second set of 4D images to generate the trained convolutional neural network.

6. The method of claim 3, wherein generating the non time-resolved CTA data comprises applying, via the processor, a weighted average to the 4D CTA data.

7. The method of claim 3, wherein generating the first and second sets of 4D images comprises performing, via the processor, 4D segmentation on the 4D CTA data.

8. The method of claim 1, wherein the trained convolutional neural network, via the processor, in reformatting the CTA image volume identifies an anatomical location of the objects of interest within the CTA image volume and determines a desired orientation of the one or more 2D CTA images.

9. A method for analyzing computed tomography angiography (CTA) data, comprising:

receiving, at a processor, four-dimensional (4D) CTA data;

generating, via the processor, non time-resolved CTA data from the 4D CTA data;

generating, via the processor, a first set of 4D images including veins only from the 4D CTA data;

generating, via the processor, a second set of 4D images including arteries only from the 4D CTA data; and training, via the processor, a convolutional neural network utilizing the non time-resolved CTA data, the first set of 4D images, and the second set of 4D images to generate a trained convolutional neural network.

10. The method of claim 9, comprising:

receiving, at the processor, three-dimensional (3D) CTA data;

automatically, via the processor, detecting objects of interest within the 3D CTA data by applying the trained convolutional neural network to the 3D CTA data to segment the objects of interest from the CTA data; and generating, via the processor, a CTA image volume that only includes the objects of interest.

11. The method of claim 10, comprising automatically, via the processor, reformatting the CTA image volume to generate one or more two-dimensional (2D) CTA images.

12. The method of claim 11, wherein automatically reformatting the CTA image volume comprises applying, via the processor, the trained convolutional neural network to the CTA image volume to reformat the CTA image volume.

13. The method of claim 12, comprising:

obtaining, at the processor, past review types utilized by users, image reformat rendering angles relative to computed tomography (CT) system landmarks for a respective past review type selected by the users, and image reformat rendering angles relative to anatomical landmarks for the respective past review type selected by the users; and training, via the processor, the convolutional neural network utilizing the past review types utilized by users, the image reformat rendering angles relative to CT system landmarks for the respective past review type selected by the users, and the image reformat rendering angles relative to anatomical landmarks for the respective past review type selected by the users to generate the trained convolutional neural network.

14. A method for analyzing computed tomography angiography (CTA) data, comprising:

obtaining, at the processor, past review types utilized by users, image reformat rendering angles relative to computed tomography (CT) system landmarks for a respective past review type selected by the users, and image reformat rendering angles relative to anatomical landmarks for the respective past review type selected by the users; and training, via the processor, a convolutional neural network utilizing the past review types utilized by users, the image reformat rendering angles relative to CT system landmarks for the respective past review type selected by the users, and the image reformat rendering angles relative to anatomical landmarks for the respective past review type selected by the users to generate a trained convolutional neural network.

15. The method of claim 14, comprising automatically, via the processor, reformatting a CTA image volume to generate one or more two-dimensional (2D) CTA images by applying the trained convolutional neural network to the CTA image volume, wherein the CTA image volume only includes objects of interest segmented from three-dimensional (3D) CTA data.

16. The method of claim 15, wherein the trained convolutional neural network, via the processor, in reformatting the CTA image volume identifies an anatomical location of the object of interest within the CTA image volume and determines a desired orientation of the one or more 2D CTA images.

17. The method of claim 15, comprising:

receiving, at the processor, the 3D CTA data;

automatically, via the processor, detecting the objects of interest within the 3D CTA data by applying the trained convolutional neural network to the 3D CTA data to segment the objects of interest from the CTA data; and generating, via the processor, the CTA image volume that only includes the objects of interest.

18. The method of claim 17, comprising:

receiving, at the processor, four-dimensional (4D) CTA data;

generating, via the processor, non time-resolved CTA data from the 4D CTA data;

generating, via the processor, a first set of 4D images including veins only from the 4D CTA data;

generating, via the processor, a second set of 4D images including arteries only from the 4D CTA data; and training, via the processor, the convolutional neural network utilizing the non time-resolved CTA data, the first set of 4D images, and the second set of 4D images to generate the trained convolutional neural network.

* * * * *